United States Patent [19]

Dixon et al.

[11] Patent Number: 4,939,129
[45] Date of Patent: Jul. 3, 1990

[54] USES OF 4-(3-PHOSPHONO-2-PROPENYL)-2-PIERAZINECARBOXYLIC ACID

[75] Inventors: Arnold K. Dixon, Neuenegg; Julian A. Gray, Binningen, both of Switzerland

[73] Assignee: Sandoz Ltd., Basel, Switzerland

[21] Appl. No.: 321,422

[22] Filed: Mar. 9, 1989

[30] Foreign Application Priority Data

Mar. 11, 1988 [GB] United Kingdom ............ 8805875
Aug. 12, 1988 [GB] United Kingdom ............ 8819192
Aug. 26, 1988 [GB] United Kingdom ............ 8820344

[51] Int. Cl.$^5$ ............................................. A61K 31/675
[52] U.S. Cl. ............................................................ 514/85
[58] Field of Search ............................................ 514/85

[56] References Cited

PUBLICATIONS

Chem. Abst. 109-211230 G (1988).
Trends in Neuroscience, 10, pp. 8–13 (1987).
Brain Research, 457, pp. 226–240 (1988).
Neurology and Neurobiology, vol. 46, pp. 661–666 (1988).

Primary Examiner—Stanley J. Friedman
Attorney, Agent, or Firm—Gerald D. Sharkin; Robert S. Honor; Joseph J. Borovian

[57] ABSTRACT

The uses of piperazinecarboxylic acid in the treatment of disorders characterized by reduced drive and/or social withdrawal, sleep disturbances or migraine.

7 Claims, No Drawings

USES OF 4-(3-PHOSPHONO-2-PROPENYL)-2-PIERAZINECARBOXYLIC ACID

The present invention relates to new pharmaceutical uses of [R-(E)]-4-(3-phosphono-2-propenyl)-2-piperazinecarboxylic acid of formula I

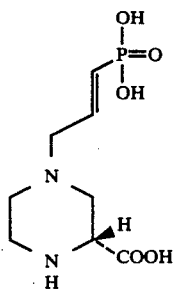

and its pharmaceutically acceptable salts.

The compound of formul I and a process for its production is described in UK Patent Application No. 2201676. The compound of formula I may form cationic and acid addition salts. Cationic salts include ammonium, sodium, potassium, calcium, piperidinium, morpholinium or pyrrolidinium salts. Acid addition salts include those formed with hydrochloric, hydrobromic, sulfuric, methanesulfonic, benzenesulfonic, p-toluenesulfonic and trifluoracetic acid. Such salts can be prepared by standard methods. The compound of formula I including its salts can also form hydrates. In a preferred embodiment the compound of formula I is in the form of its monohydrate.

In accordance with the present invention it has now surprisingly been found that the compound of formula I promotes social interactions and approach-oriented activities in mice in the intruder-test [A. K. Dixon, Triangle 21, 95–105 (1982); A. K. Dixon, H. P. Kaesermann: "Ethopharmacology of flight behaviour" in: Ethopharmacology of Agonistic Behaviour in Animals and Humans, ed. Olivier B. Mos J. Brain PF (1987) Martinus Nijhoff Publishers, Dordrecht 46–79]. Groups of 8 male mice (OF-1, Sandoz Basel) per dose are used. All observations are performed under red light. In this test the compound of formula I in a dose of 0.3–3 mg/kg p.o. causes and increase in the frequencies and durations of social investigation (SI), thereby counteracting the social withdrawal engendered by the situation.

In view of its augmenting effects on social interactions the compound of formula I is useful in the treatment of disorders characterized by reduced drive and/or social withdrawal primarily in elderly subjects.

For this indication the appropriate dosage will, of course, vary depending upon, for example, the host, the mode of administration and the nature and severity of the condition being treated. However, in general, satisfactory results in animals are indicated to be obtained at a daily dosage of from about 0.3 to about 3 mg/kg animal body weight. In larger mammals, for example humans, an indicated daily dosage is in the range from about 5 to about 800 mg of the compound of formula I conveniently administered, for example, in divided doses up to four times a day.

The present invention also provides the compound of formula I or a pharmaceutically acceptable salt thereof for use in the treatment of disorderes characterized by reduced drive and/or social withdrawal.

The present invention accordingly provides a method for treatment of disorders characterized by reduced drive and/or social withdrawal in a subject in need of such treatment which comprises administering to said subject a therapeutically effective amount of the compound of formula I or a pharamaceutically acceptable salt thereof. Such salts exhibit the same order of activity as the compound of formula I. The invention also provides pharmaceutical compositions comprising the compound of formula I or a pharmaceutically acceptable salt thereof for use in the treatment of disorders characterized by reduced drive and/or social withdrawal. Such compositions may be formulated in conventional manner, so as to be for example a tablet or a solution.

In accordance with the present invention it has furthermore surprisingly been found that the compound of formula I has sleep enhancing e.g. sleep-inducing and sleep-promoting activity. This can be shown in the sleep-EEG in the rat using e.g. the cable recording technique described by H. Kleinlogel. and al., Waking and Sleeping 4, 77–85 (1980):

The study is carried out using 4 male rats (Wistar). The animals (3 to 4 months old) are anaesthetized with pentobarbital-sodium (Nembutal, Abbot, 50 mg/ml), 50 mg/kg i.p. in 1 ml 0.9% NaCl. Following abolition of the pinna reflex the head is shaved and fixed in a stereotactic instrument. After exposing the skull, the electrodes are implanted: 2 EEG recording electrodes are inserted over the frontal cortex (the coordinates are lateral 2 mm and anterior 2 mm from the bregma), 2 electrodes over the occipital cortex (lateral 2 mm and anterior 2 mm from the lambda), an indifferent electrode over teh cerebellum (lateral 0.5 mm and posterior 2 mm from the lambda) and an electrode in the neck muscles to obtain an electromyogram (EMG). In all cases the electrodes are silvered brass screws with a winding length of 2.5 mm, a winding diameter of 0.65 mm and a head diameter of 1.5 mm. The insertion depth is only 1 mm. The various electrodes are then connected by silver wires to the pins of the miniplug. After this procedure, the skull, electrodes and miniplug are covered with methyl methacrylate (Paladur, Kulzer, Bad Homburg, West Germany). After suturing the wound the rat is given a subcutaneous injection of 0.1 ml streptomycine-sulfate (690 units/mg, Sigma AG).

Recordings are carried out 7-8 months after electrode implantation. During recording sesssions the rats are housed in the same cages as between sessions. However, and additional outer box is used to protect against electrical and acoustic interference from outside. The animals are maintained on 24 hours light-dark cycle (light from 8.00 to 20.00) at an ambient temperature of 22°±3° C. and a humidity of 40–70%. Water and food are available and libitum. EEG recordings are made simultaneously from 4 rats using a 16 channel Minograph EEG (Siemens-Elema). From each rat monopolar derivations from the right frontal and occipital cortices as well as the EMG from the posterior muscles are obtained. An additional occipital derivation is filtered above 10 Hz. The transformation of the EMG is carried out by a frequency-voltage-converter. 4 days before administration of the drug the rats are given orally 5 ml/kg tap-water by stomach tube. The same rats receive then intragastrically the compound of formula I in distilled water once every 3–4 days in increasing dosages. The solutions are clear and are given about 15 minutes before recording. Recordings are made during 6 hours (from 9.00 until 15.00). Additionally with the aid of a computer (IBM Personal Computer, XT Model 286) the power spectra of EEG and EMG during consecutive 8 sec epochs on line are computed using Fast Fourier Transformation. The initial resolution is 0.25 Hz. Immediately after the experiment the EEG data are reduced into frequency bands covering a frequency range from 1 to 32 Hz. With the aim of the reduced power-spectra the following stages of wakefulness and sleep are differentiated:

(1) Wakefulness with active EMG (WS I)
(2) Wakefulness without active EMG (WS II)
(3) Classical sleep I (KLS I)
(4) Classical sleep II (KLS II)
(5) Paradoxical sleep (PS).

Each animal serves as its own control. The compound of formula I is tested at dosages of 3.2, 10 and 32 mg/kg p.o.

During the first 3 hours recording 3.2 mg/kg p.o of the compound increases significantly paradoxial sleep. There is further a shift from classical sleep II to classical sleep I. Administration of 10 mg/kg alters all stages significantly: WS I and KLS II are reduced; WS II, KLS I and PS are increased.

After 6 hours recording with 3.2 mg/kg all stages except WS II are significantly altered: WS I and KLS II are reduced, KLS I and PS are increased. After administration of 10 resp. 32 mg/kg these effects are quantitatively more pronounced.

The compound of formula I can therefore be used in the treatment of sleep disturbances.

For this indication the appropriate dosage will, of course, vary depending upon, for example, the host, the mode of administration and the nature and severity of the condition being treated. However, in general, satisfactory results in animals are indicated to be obtained at a daily dosage of from about 3 to about 10 mg/kg animal body weight. In larger mammals, for example humans, an indicated daily dosage is in the range from about 5 to about 800 mg of the compound of formula I conveniently administered shortly before retiring to sleep.

The present invention accordingly provides the compound of formula I or a pharmaceutically acceptable salt thereof for use in the treatment of sleep disturbances.

The present invention further provides a method for the treatment of sleep disturbances in a subject in need of such treatment which comprises administering to said subject a therapeutically effective amount of the compound of formula I or a pharmaceutically acceptable salt thereof.

Such salts exhibit the same order to activity as the compound of formula I. The invention also provides pharamaceutical compositions comprising the compound of formula I or a pharmaceutically acceptable salt thereof for use in the treatment of sleep disturbances. Such compositions may be formulated in conventional manner, so as to be for example a tablet or a solution.

Additionally the compound of formula I exhibits spreading depression inhibiting activity in the frontal cortex of rats [R. Marrannes et al., Brain Research 457 (1988)226]. In this test the compound increases spreading depression threshold and propagation time and reduces spreading depression duration at a dosage of from 3 to 30 mg/kg i.p.

The compound of formula I is, therefore, useful in the treatment of migraine, e.g. classical migraine.

For this indication the appropriate dosage will, of course, vary depending upon, for example, the host, the mode of administration and the nature and severity of the condition being treated. However, in general, satisfactory results in animals are indicated to be obtained at a daily dosage of from about 3 to about 30 mg/kg animal body weight. In larger mammals, for example humans, an indicated daily dosage is in the range from about 5 to about 800 mg of the compound of formula I conveniently administered, for example, in divided doses up to four times a day.

The present invention accordingly provides the compound of formula I or a pharmaceutically acceptable salt thereof for use in the treatment of migraine.

The present invention accordingly provides a method for the treatment of migraine in a subject in need of such treatment which comprises administering to said subject a therapeutically effective amount of the compound of formula I or a pharmaceutically acceptable salt thereof. Such salts exhibit the same order of activity as the compound of formula I. The invention also provides pharmaceutical compositions comprising the compound of formula I or a pharmaceutically acceptable salt thereof for use in the treatment of migraine. Such compositions may be formulated in conventional manner, so as to be for example a tablet or a solution.

The compound of formula I may be administered by any conventional route, in particular enterally, preferably orally e.g. in the form of tablets or capsules, or parenterally, e.g. in the form of injectable solutions or suspensions.

A unit dosage may contain from about 0.25 to about 400 mg of the compound of formula I or a hydrate thereof or a pharmaceutically acceptable salt thereof.

The pharmaceutical compositions can be prepared according to conventional techniques.

The present invention further provides the use of the compound of formula I or a pharmaceutically acceptable salt thereof for the manufacture of a pharmaceutical composition for treating disorders characterized by reduced drive and/or social withdrawal, sleep disturbances or migraine.

We claim:

1. A method of treating disorders characterized by reduced drive and/or social withdrawal comprising administering to a subject in need of such treatment a therapeutically effective amount of the compound of formula I

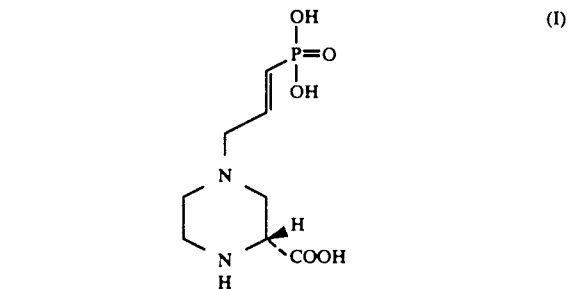

or a pharmaceutically acceptable acid addition salt thereof, or a corresponding hydrate thereof.

2. A method of claim 1 wherein the compound of formula I is administered in monohydrate form.

3. A method of treating sleep disturbances comprising administering to a subject in need of such treatment a therapeutically effective amount of the compound of formula I

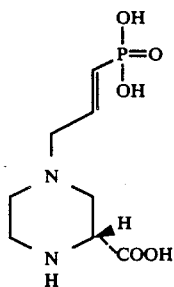
(I)

or a pharmaceutically acceptable acid addition salt thereof, or a corresponding hydrate thereof.

4. A method of claim 3 wherein the compound of formula I is administered in monohydrate form.

5. A method of treating migraine headaches comprising administering to a subject in need of such treatment a therapeutically effective amount of the compound of formula I

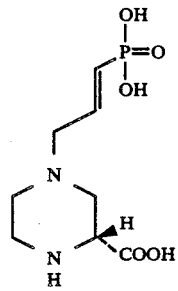
(I)

or a pharmaceutically acceptable acid addition salt thereof, or a corresponding hydrate thereof.

6. A pharmaceutical composition for use in treating disorders characterized by reduced drive and/or social withdrawal, sleep disturbances or migraine headaches comprising a pharmaceutically acceptable carrier or diluent and a therapeutically effective amount of the compound of formula I

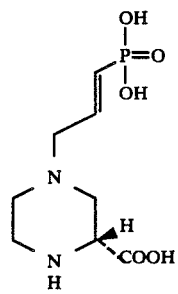
(I)

or a pharmaceutically acceptable acid addition salt thereof, or a corresponding hydrate thereof.

7. A composition according to claim 6 wherein the compound of formula I is in monohydrate form.

* * * * *